(12) United States Patent
Neal et al.

(10) Patent No.: US 11,246,576 B2
(45) Date of Patent: Feb. 15, 2022

(54) BIOPSY PUNCH DEVICE AND METHOD

(71) Applicant: University of Kansas, Lawrence, KS (US)

(72) Inventors: Christopher Neal, Kansas City, MO (US); Adam J. Mellott, Olathe, KS (US); David S. Zamierowski, Overland Park, KS (US)

( * ) Notice: Subject to any disclaimer, the term of this patent is extended or adjusted under 35 U.S.C. 154(b) by 479 days.

(21) Appl. No.: 15/913,773

(22) Filed: Mar. 6, 2018

(65) Prior Publication Data

US 2018/0249988 A1 Sep. 6, 2018

Related U.S. Application Data

(60) Provisional application No. 62/467,453, filed on Mar. 6, 2017.

(51) Int. Cl.
*A61B 10/02* (2006.01)

(52) U.S. Cl.
CPC ...... *A61B 10/0275* (2013.01); *A61B 10/0266* (2013.01); *A61B 2010/0208* (2013.01)

(58) Field of Classification Search
CPC ............ A61B 10/0275; A61B 10/0266; A61B 2010/0208
USPC ...................................................... 600/567
See application file for complete search history.

(56) References Cited

U.S. PATENT DOCUMENTS

| 3,683,892 A | 8/1972 | Harris |
| 4,210,145 A | 7/1980 | Nestor et al. |
| 4,832,045 A * | 5/1989 | Goldberger ........ A61B 10/0233 600/567 |
| 7,481,775 B2 | 1/2009 | Weikel, Jr. et al. |
| 8,540,646 B2 * | 9/2013 | Mendez-Coll ..... A61B 10/0233 600/562 |
| 2008/0077146 A1 | 3/2008 | Pernsteiner et al. |
| 2013/0096458 A1 | 4/2013 | Schraga |
| 2014/0128769 A1 | 5/2014 | Vetter |

(Continued)

FOREIGN PATENT DOCUMENTS

| WO | 2015056226 | 4/2015 | |
| WO | WO-2017180761 A1 * | 10/2017 | ............. A61B 10/02 |

*Primary Examiner* — David J. McCrosky
*Assistant Examiner* — Chanel J Jhin
(74) *Attorney, Agent, or Firm* — Law Office of Mark Brown, LLC; Mark E. Brown

(57) ABSTRACT

A biopsy punch device and method for making punch cuts at consistent predetermined depths. In an exemplary embodiment of the biopsy punch device includes two interconnecting pieces: an inner housing piece and an outer blocking cover piece. The inner housing piece releasably mounts cutting blades arranged in a desired geometric shape for biopsy punch cuts. The blocking cover piece overlays the inner housing piece in an assembled configuration and includes two openings: a larger distal end opening and a narrower proximal end cutting blade opening. The blocking cover distal end opening fits around and adjacent to the housing piece distal end. The blocking cover proximal end opening fits around and adjacent to the cutting blades. With the biopsy punch device in assembled position, the proximal side of the blocking cover piece provides a mechanical stop in the cutting process at the desired depth of penetration of the cutting blades.

14 Claims, 20 Drawing Sheets

(56) References Cited

U.S. PATENT DOCUMENTS

2015/0057572 A1 2/2015 Mendez-Coll et al.
2015/0105690 A1* 4/2015 Hathaway .......... A61B 10/0275
600/566

* cited by examiner

BIOPSY PUNCH DEVICE AND METHOD

CROSS-REFERENCE TO RELATED APPLICATIONS

This application claims priority in U.S. Provisional Patent Application No. 62/467,453, filed Mar. 6, 2017, which is incorporated herein by reference.

BACKGROUND OF THE INVENTION

1. Field of the Invention

The present invention relates generally to biopsy punch devices and methods. More particularly, the present invention relates to a device and method for shape and depth-controlled biopsies of human and animal tissue for medical diagnosis and/or research purposes.

2. Description of the Related Art

A biopsy is the extraction of tissue from a living organism and the examination of that tissue for the presence of different biological conditions. Biopsy tissue samples are often an integral aspect of medical testing and diagnosis of various diseases and medical conditions. Further, biopsy tissue samples are commonly used in biomedical and clinical research, including those with animal testing and human testing, to determine the effectiveness and viability of different medical treatments.

Depending largely on the particular type of tissue to be extracted and/or the medical conditions to be tested, the size of biopsy tissue samples vary, ranging from small needle biopsies to larger, punch skin biopsies. For biopsies testing punch-type tissue samples, particularly those for medical research, it can be very important for biopsy tissue samples to be of a precise and reproducible size to produce useful, comparable results.

Currently, most punch biopsy tools available include a circular cutting blade designed for obtaining cylindrical tissue samples. Many of these punch biopsy devices accommodate reproducible tissue sample sizes with precise cutting blade measurements and a fixed cutting depth. However, it can be difficult to find biopsy punch devices having a circular cutting blade larger than 8 millimeters in diameter. For many medical research products, such as those involving testing the effects of medical treatments on animal tissue, it is desirable to test larger tissue samples than cylinder-shaped biopsy tissue samples having an 8 millimeter diameter. This can make readily available punch biopsy tools impractical for obtaining the most useful results. Additionally, generally speaking, the larger the cutting blade, the more expensive the biopsy punch tool. Most biopsy punch devices are disposal, requiring a new device for each biopsy tissue sample. Nonetheless, even reusable biopsy punch devices can be a large expense because replacing cutting blades or entire punch devices when the blades become dull or contaminated can be expensive. Medical research requiring numerous trials of biopsy punch tissue samples would particularly benefit from an inexpensive and easily scalable biopsy punch device option which produces consistent, reproducible biopsy tissue samples.

While some currently available biopsy punch devices have adjustable depth parameters for adjusting the thickness or depth of cuts, these adjustable biopsy punch devices commonly include threaded depth adjustment mechanisms, which increase or decrease the cutting depth based on the direction a piece of the device is turned or twisted. Such threaded adjustment can be imprecise. For instance, the adjustment piece may unintentionally be turned one way or another when in use. Also, the depth could inadvertently be pushed deeper during the process of making a punch cut, especially if the device is turned by the user when making the cut. What is desired is a cost-effective biopsy punch device having multiple precise depth adjustment settings with locking features to lock the precise cutting depth in place.

Heretofore, there has not been available a biopsy punch device and method with the advantages and features of the present invention.

SUMMARY OF THE INVENTION

The present invention provides a biopsy punch device and method for making punch cuts at consistent, predetermined thicknesses or depths. In the practice of an aspect of the present invention, the biopsy punch device includes two interconnecting pieces: an inner housing piece and an outer blocking cover piece. The inner housing includes a wider distal end and a narrower proximal end with a mounting portion having a plurality of connection slots for removably mounting cutting blades arranged in a desired shape for biopsy punch cuts.

The blocking cover piece is configured to overlay the inner housing piece in an assembled configuration and includes two openings: a larger distal end opening and a narrower proximal end cutting blade opening. The blocking cover distal end opening is configured to fit around and adjacent to the housing piece distal end. The blocking cover proximal end opening is configured to fit around and adjacent to the cutting blades. The blocking cover proximal end further holds the cutting blades in fixed position within the connection slots and up against the mounting portion of the housing.

In an aspect of the present invention, the biopsy punch device includes a locking mechanism having at least one locking position for releasably locking the blocking cover piece in a desired position in relation to the inner housing piece and cutting blades. In some embodiments, the biopsy punch device includes multiple locking position settings, making the device adjustable to multiple desired depth or thickness settings. With the biopsy punch device in assembled position, the proximal side of the blocking cover piece provides a mechanical stop in the cutting process at the desired depth of penetration of the cutting blades. This accommodates consistent punch cuts at predetermined thicknesses.

Embodiments of the biopsy punch device include a variety of shapes, sizes of cutting blades, and cutting depths, depending on the desired shape and size of tissue samples to be cut. In each embodiment, the cutting blades are configured for being easily replaced. In exemplary embodiments, the inner housing piece and blocking cover piece are three-dimensionally modeled on a computing device and formed by additive manufacturing. Such embodiments allow biopsy punch devices of the present invention to be easily scaled larger or smaller and the arrangement of cutting blade connection slots and the housing mounting portion to be easily modified.

BRIEF DESCRIPTION OF THE DRAWINGS

The drawings constitute a part of this specification and include exemplary embodiments of the present invention illustrating various objects and features thereof.

DETAILED DESCRIPTION OF THE PREFERRED EMBODIMENTS

I. Introduction and Environment

Figure 1:
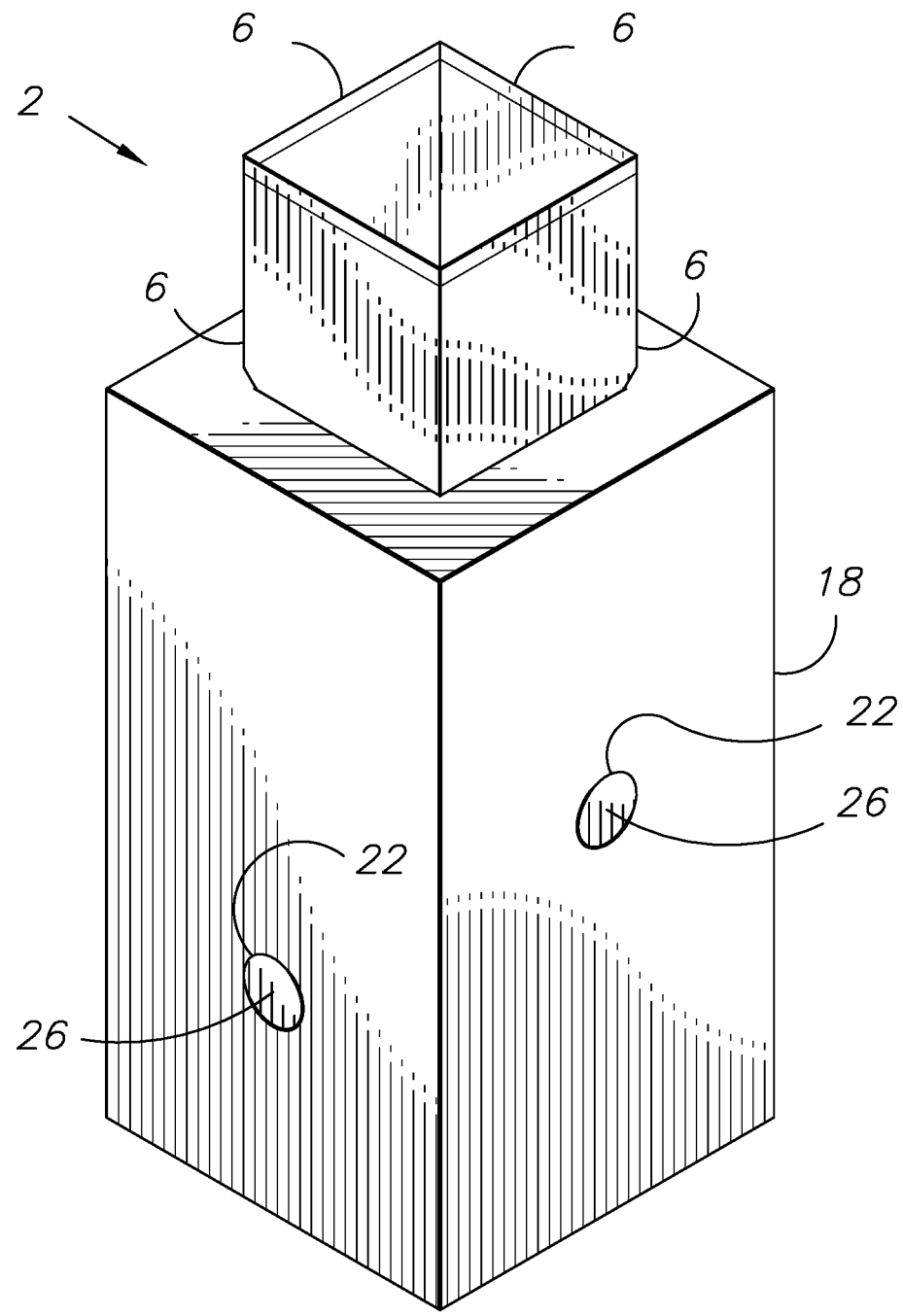
FIG. 1 is an upper, perspective, assembled view of a biopsy punch device embodying the present invention.

As required, detailed aspects of the present invention are disclosed herein, however, it is to be understood that the disclosed aspects are merely exemplary of the invention, which may be embodied in various forms. Therefore, specific structural and functional details disclosed herein are not to be interpreted as limiting, but merely as a basis for the claims and as a representative basis for teaching one skilled in the art how to variously employ the present invention in virtually any appropriately detailed structure.

Certain terminology will be used in the following description for convenience in reference only and will not be limiting. For example, up, down, front, back, right, and left refer to the invention as orientated in the view being referred to. The words, "inwardly" and "outwardly" refer to directions toward and away from, respectively, the geometric center of the aspect being described and designated parts thereof. Forwardly and rearwardly are generally in reference to the direction of travel, if appropriate. Additionally, anatomical terms are given their usual meanings. For example, proximal means closer to the trunk of the body, and distal means further from the trunk of the body. Said terminology will include the words specifically mentioned, derivatives thereof and words of similar meaning.

II. Preferred Embodiment Biopsy Punch Device

An exemplary embodiment of the present invention provides a biopsy punch device 2 configured for cutting one or more tissue samples 32 in a desired, three-dimensional, prism shape at a consistent, predetermined thickness or depth. In this embodiment, the biopsy punch device 2 includes two interconnecting pieces: an inner housing piece 4 and an outer blocking cover piece 18. The inner housing piece 4 is configured for receiving and releasably mounting cutting blades 6 arranged in a desired shape. The blocking cover piece 18 is configured to overlay the inner housing piece 4, to further hold the cutting blades 6 in mounted position, and to provide a mechanical stop or block at a desired cutting depth or thickness.

The housing piece 4 and blocking cover piece 18 are configured to be made of a rigid material, and these pieces can be made of the same material or different materials. The housing and blocking cover pieces 4, 18 may be made up of rigid plastics, metals, ceramics, or any other rigid material capable of holding cutting blades 6 and mechanically stopping a punch cut. These pieces may be made up of solid material or, alternatively, may be composed internally of material in another configuration, such as a honeycomb lattice configuration, which retains rigid strength. In a preferred embodiment, the housing 4 and blocking cover 18 pieces can be three-dimensionally modeled with computer-aided design on a computing device and produced, or printed, by additive manufacturing with filaments, such as but not limited to acrylonitrile butadiene styrene (ABS), polylactic acid (PLA), or nylon filament. Such embodiments allow for biopsy punch devices 2 of the present invention to be easily scaled larger or smaller and modified for different cutting blade 6 arrangement shapes. Other embodiments of the present invention can be produced by other manufacturing methods, such as subtractive manufacturing, injection molding, etc.

The inner housing piece 4 includes a wider distal end 16 and a narrower proximal end 15. The housing proximal end 15 includes a cutting blade mounting portion 12 having a series of cutting blade connection or receiving slots 10 configured for receiving and holding a cutting blade 6 against each side of the mounting portion 12. With the cutting blades 6 mounted in the connection slots 10, the mounting portion 12 extends proximally a partial length of the cutting blades 6, on the inside of the blades 6, to further hold the blades 6 in proper assembled position. In an exemplary embodiment, the cutting blades 6 are single-edge razorblades of a readily available size having one sharpened edge. In a preferred embodiment, the razorblades include a notch 8 opposite the sharpened cutting edge, and the connection slots 10 are configured to receive and hold the razorblade notched end 8. Readily available razorblades, preferably notched razorblades, may also be cut to size, as desired, for use with the present invention. Most commonly, cutting blades 6 of the present invention are made of stainless steel, but other metals or capable cutting materials may alternatively be used. Use of standard, readily available razorblades in connection slots 10 allows the cutting blades 6 of the present invention to be easily and inexpensively replaced.

The blocking cover piece 18 includes two openings: a larger distal end opening 24 and a narrower proximal end opening 20. The blocking cover distal end opening 24 is configured for fitting over and adjacent to the inner housing piece distal end 16. The blocking cover proximal end opening 20 is configured for fitting around and adjacent to the inner housing mounting portion 12 and the cutting blades 6. The narrower proximal end opening 20 of the blocking cover 18 further holds the cutting blades 6 in place between the mounting portion 12 and the blocking cover 18. The present invention further includes a releasable locking mechanism for holding the blocking cover 18 in proper position in relation to the inner housing 4 and cutting blades 6 in an assembled position. The locking mechanism may include, but is not limited to, grooves and pins; one or more snapping actuators; an internal shelf receiver portion of the inner housing and step or stopper portion of the blocking cover; magnets; hooks; or any other type of releasable locking mechanism.

With the biopsy punch device 2 in assembled position, with the blocking cover piece 18 locked in place in proper relation to the inner housing piece 4 and cutting blades 6, the proximal side of the blocking cover 18 provides a mechanical stop in the cutting process at the desired cutting depth or thickness. In assembled position, the cutting blades 6 are exposed proximally beyond the blocking cover 18 proximal side a length equal to the desired depth or thickness of biopsy tissue sample 32 to be cut. In use, the blocking cover piece 18 proximal side makes contact with tissue immediately outside of the tissue being cut by the cutting blades 6, causing the depth of penetration of the cutting blades 6 to stop at the desired depth of biopsy tissue sample 32. In some embodiments, the proximal side of the inner housing mounting portion 12 may be coplanar with the proximal side of the blocking cover piece 18 in assembled position, providing an additional mechanical stop feature. Further, in alternative embodiments, the proximal side of the inner housing mounting portion 12 may be configured to act as the primary mechanical stop feature of the biopsy punch device 2.

Figure 20:
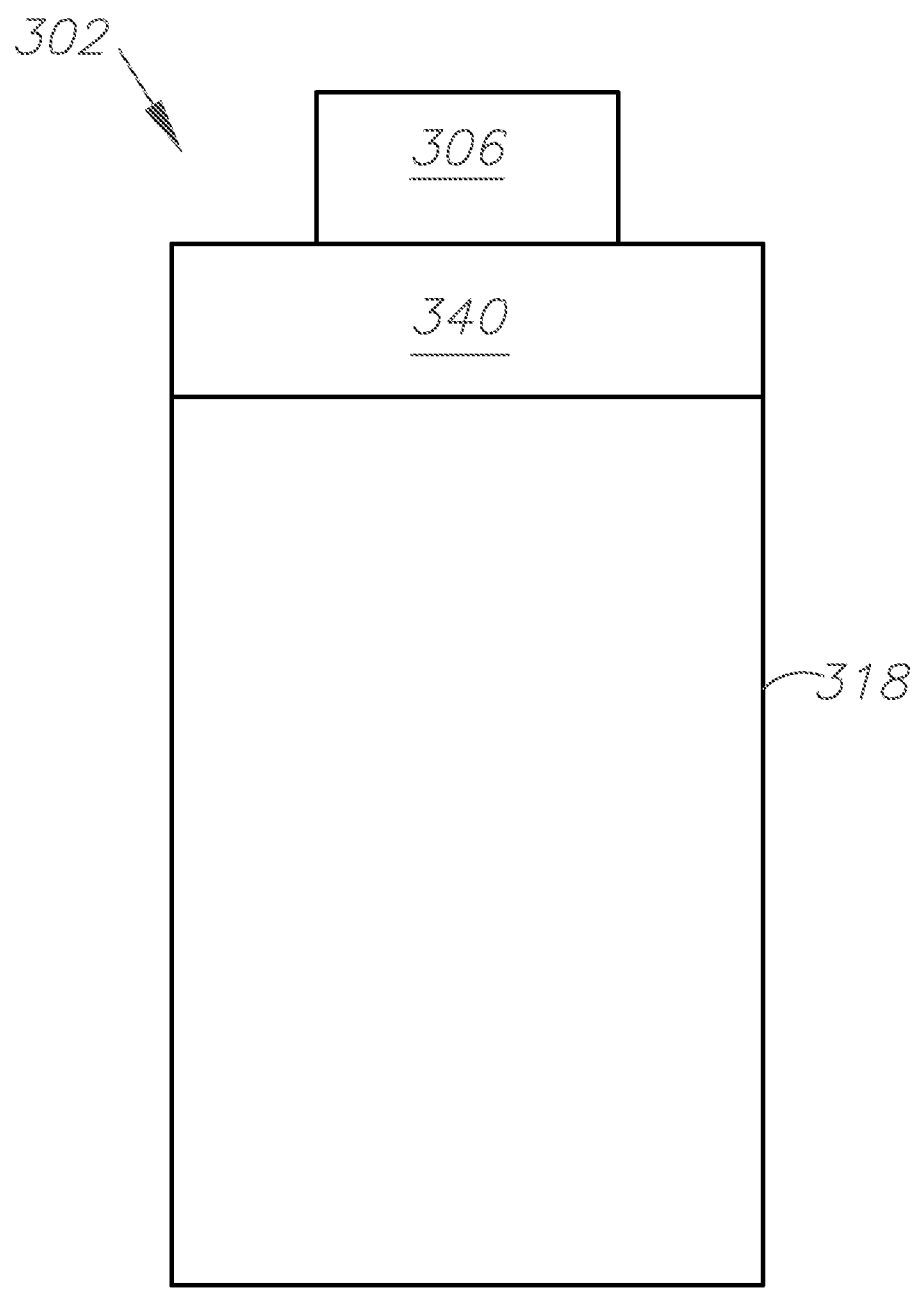
FIG. 20 is a side, elevational view of an embodiment of a biopsy punch device of the present invention including a blocking cover extension attachment.

In an exemplary embodiment of the present invention, the biopsy punch device 2 includes multiple adjustment settings for fixed positions of the blocking cover 18 proximal end in relation to the cutting blades 6. Embodiments may include multiple grooves and pins; multiple snapping actuators, multiple hooks; etc. An alternative embodiment includes one or more separate blocking cover extension attachments 340, as shown in FIG. 20, which attach to the blocking cover piece proximal end around and adjacent to the cutting blades, exposing predetermined fixed depths of the cutting blades when assembled. Embodiments of such blocking cover extension attachments 340 may attach by grooves and pins; snapping actuators; magnets; hooks; etc. In some embodiments, blocking cover attachments 340 may be simply held in place by a user.

The present invention can be configured for mounting cutting blades 6 in a variety of shapes and sizes and with a variety of cutting depths. Particularly, embodiments including inner housing 4 and blocking cover 18 pieces printed by additive manufacturing, or three-dimensional printing, coupled with readily available notched razorblades, provide an effective and inexpensive biopsy punch device 2 and method for cutting consistent, fixed-depth punch biopsy tissue samples 3. Embodiments include punch devices 2 with cutting blades 6 arranged in squares, triangles, rectangles, parallelograms, pentagons, hexagons, octagons, any other polygons, and any other shapes having straight sides. The widths of the cutting blades 6, and thus the sides of the geometric shape, may all be equal or different sizes. The more sides with cutting blades 6 of equal widths, the closer the cutting blade 6 arrangements are to a circle. Thus, embodiments of the present invention having a higher number of sides provide very close, cheaper, and effective alternatives to circular biopsy punches. Additional embodiments include paired blades set at specified distances apart configured for cutting strips. Paired blades may be lined up or offset to achieve an oblique base when a cut strip is removed along a pre-cut depth. Further embodiments of the present invention may include biopsy punch devices with circular, elliptical, or ovoid cutting blades with adjustable depth settings. The invention could also be adapted for a needle biopsy or a single straight blade having a blocking feature with fixed depth settings.

Referring to the drawings in more detail, FIGS. 1-12 show an exemplary embodiment of the present invention having cutting blades 6 arranged in a square shape. This embodiment comprises a biopsy punch device 2 configured to produce cubic tissue punch biopsy samples 32 with a fixed depth of penetration of the cutting blades 6 equal to each side length of the square shape. The biopsy device 2 of this embodiment includes an inner housing piece 4 and a blocking cover piece 18 configured to overlay the housing piece 4. The inner housing piece 4 includes a wider distal end 16 and a narrower proximal end 15 having a mourning portion 12. The mounting portion 12, in this embodiment, is in a square shape and includes four connection or receiving slots 10, one on each side of the square, for receiving and holding four cutting blades 6 arranged in a square-shaped configuration.

Figure 2:
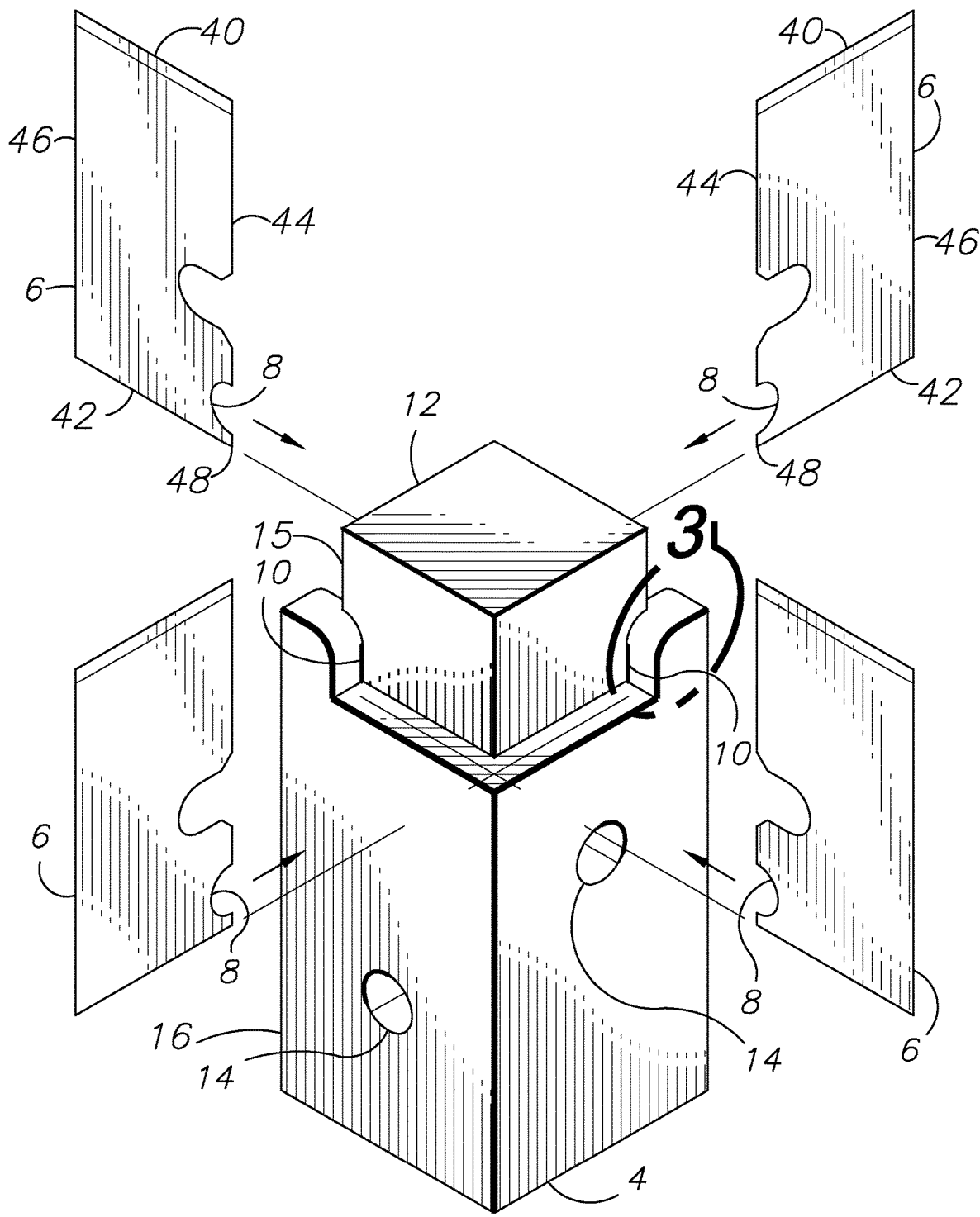
FIG. 2 is an upper, perspective, exploded view of an inner housing piece and cutting blades of the biopsy punch device.
Figure 3:
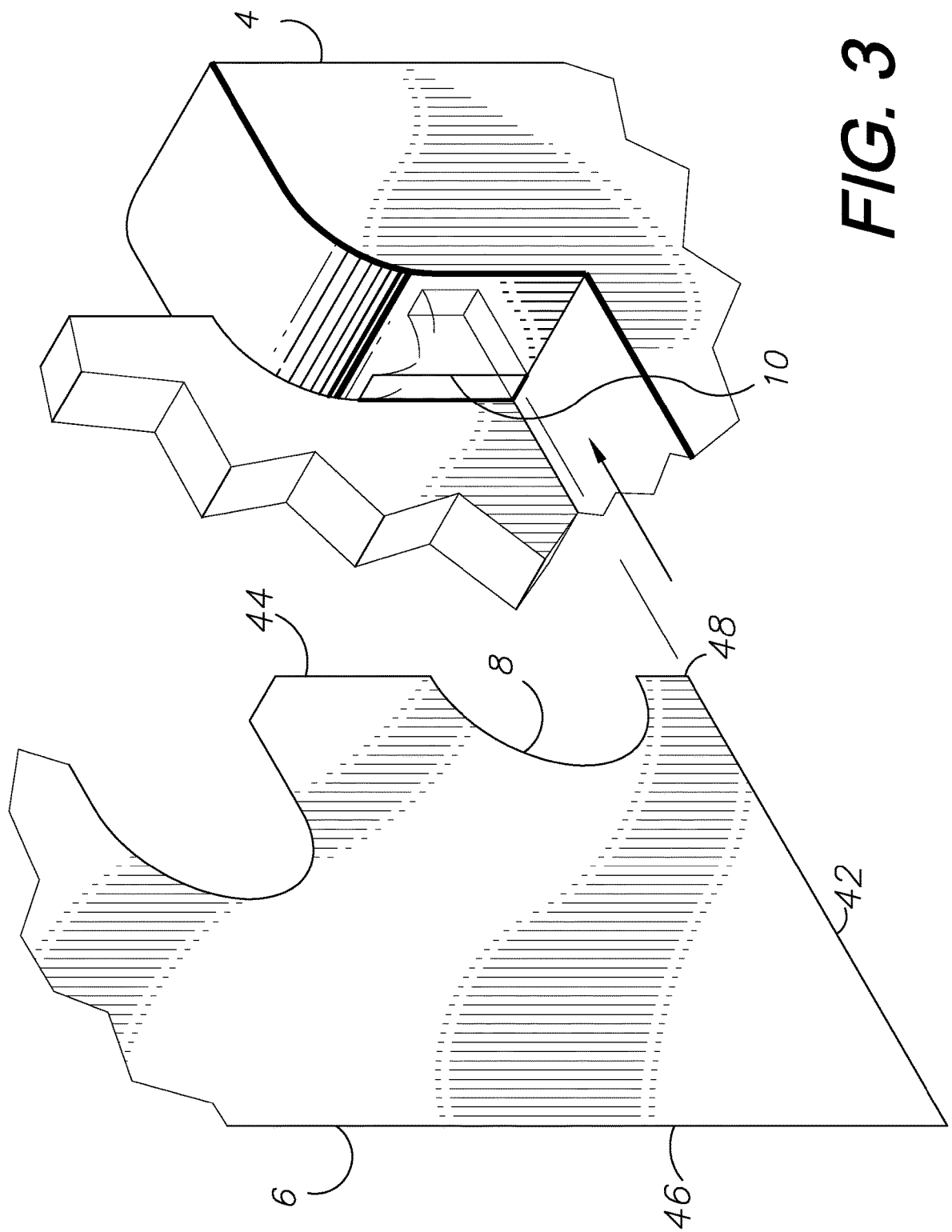
FIG. 3 is a perspective, enlarged, sectional view of a connection slot of the inner housing piece and a cutting blade notch embodying an aspect of the present invention.
Figure 4:
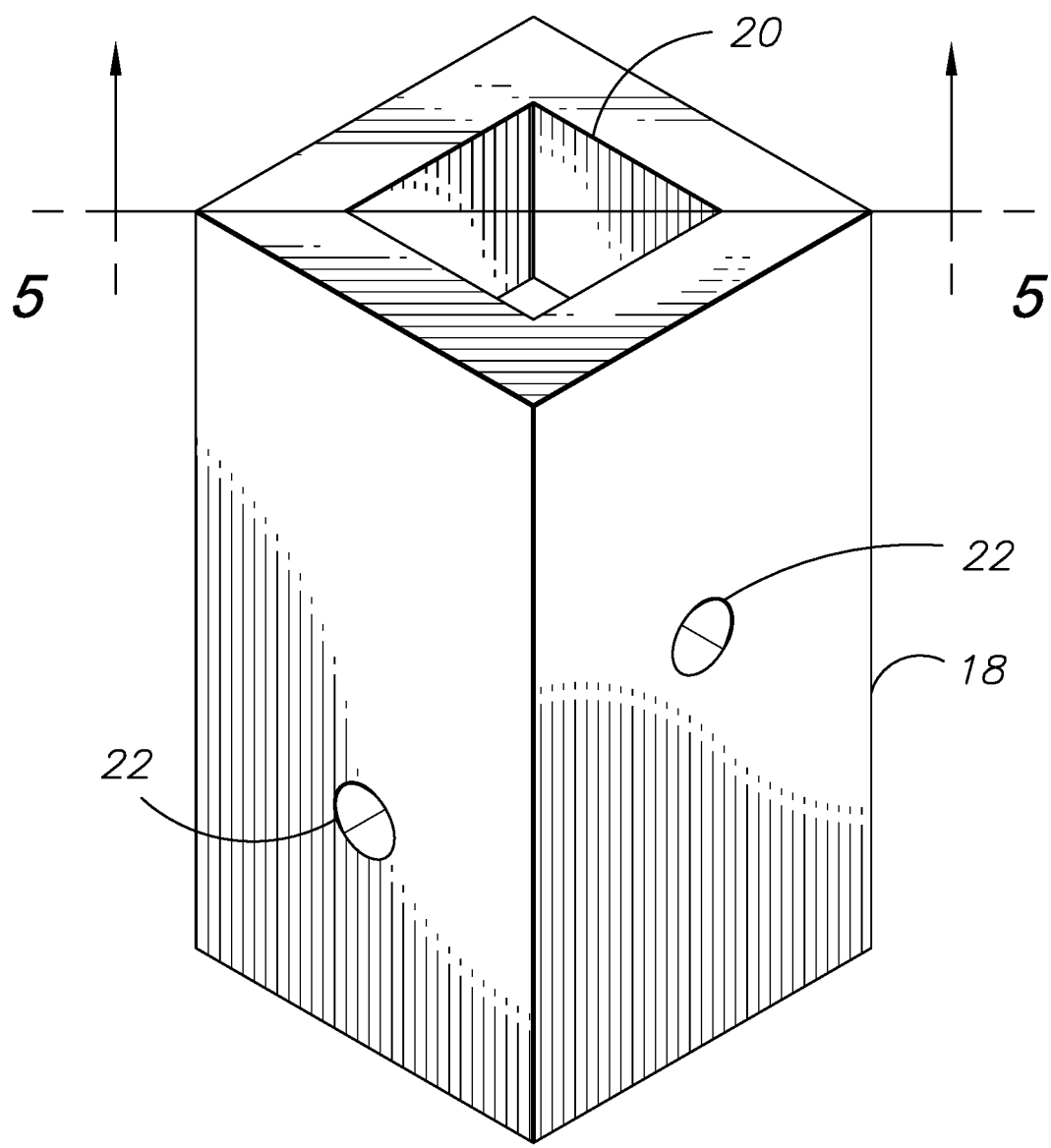
FIG. 4 is an upper, perspective view of a blocking cover piece of the biopsy punch device.
Figure 5:
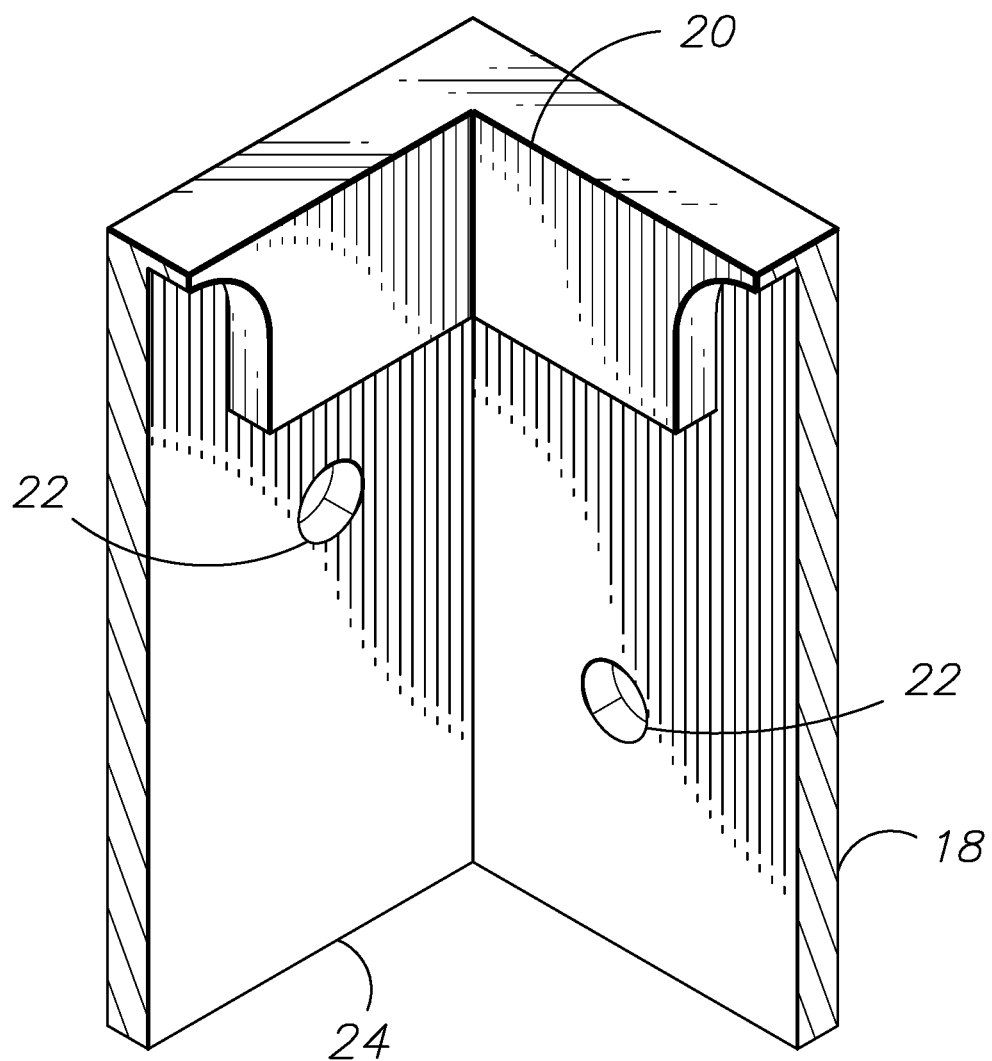
FIG. 5 is an upper, perspective, cross-sectional view of the blocking cover piece.
Figure 6:
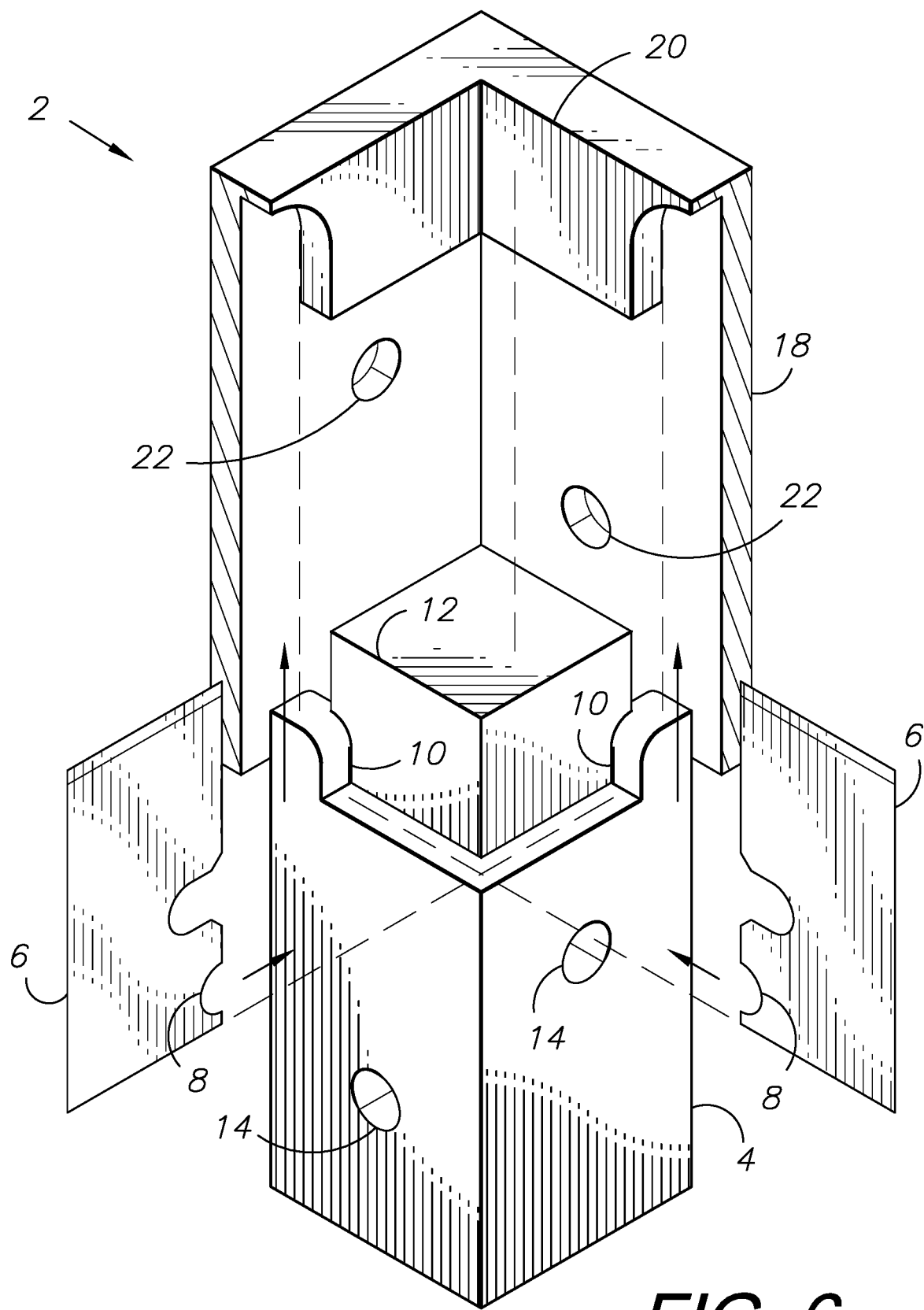
FIG. 6 is an upper, perspective, exploded, cross-sectional view of an inner housing piece, cutting blades, and a blocking cover piece of the biopsy punch device.
Figure 7:
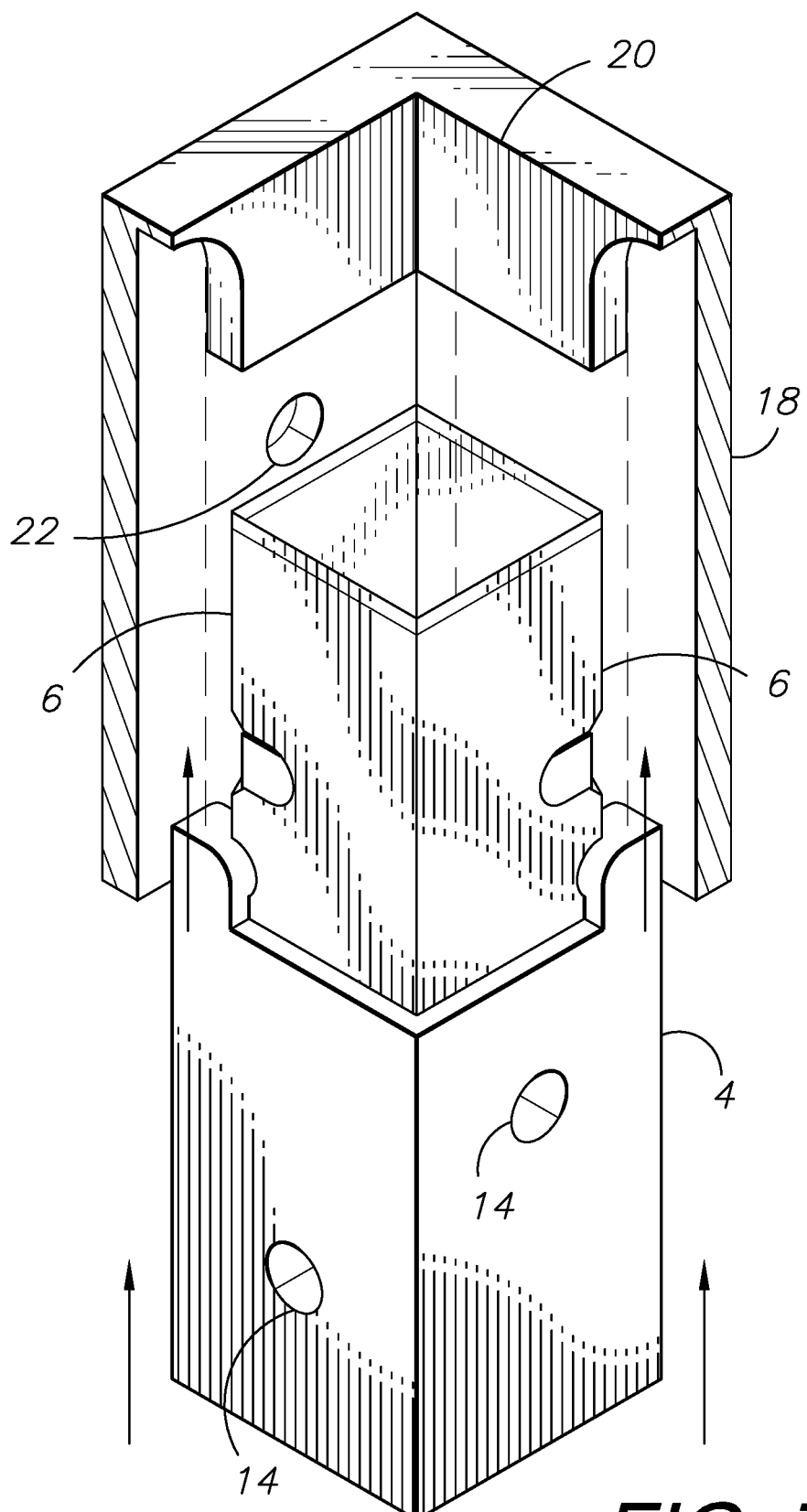
FIG. 7 is an upper, perspective, exploded, cross-sectional view of the inner housing piece, cutting blades, and blocking cover piece, with the cutting blades assembled into the inner housing piece.
Figure 8:
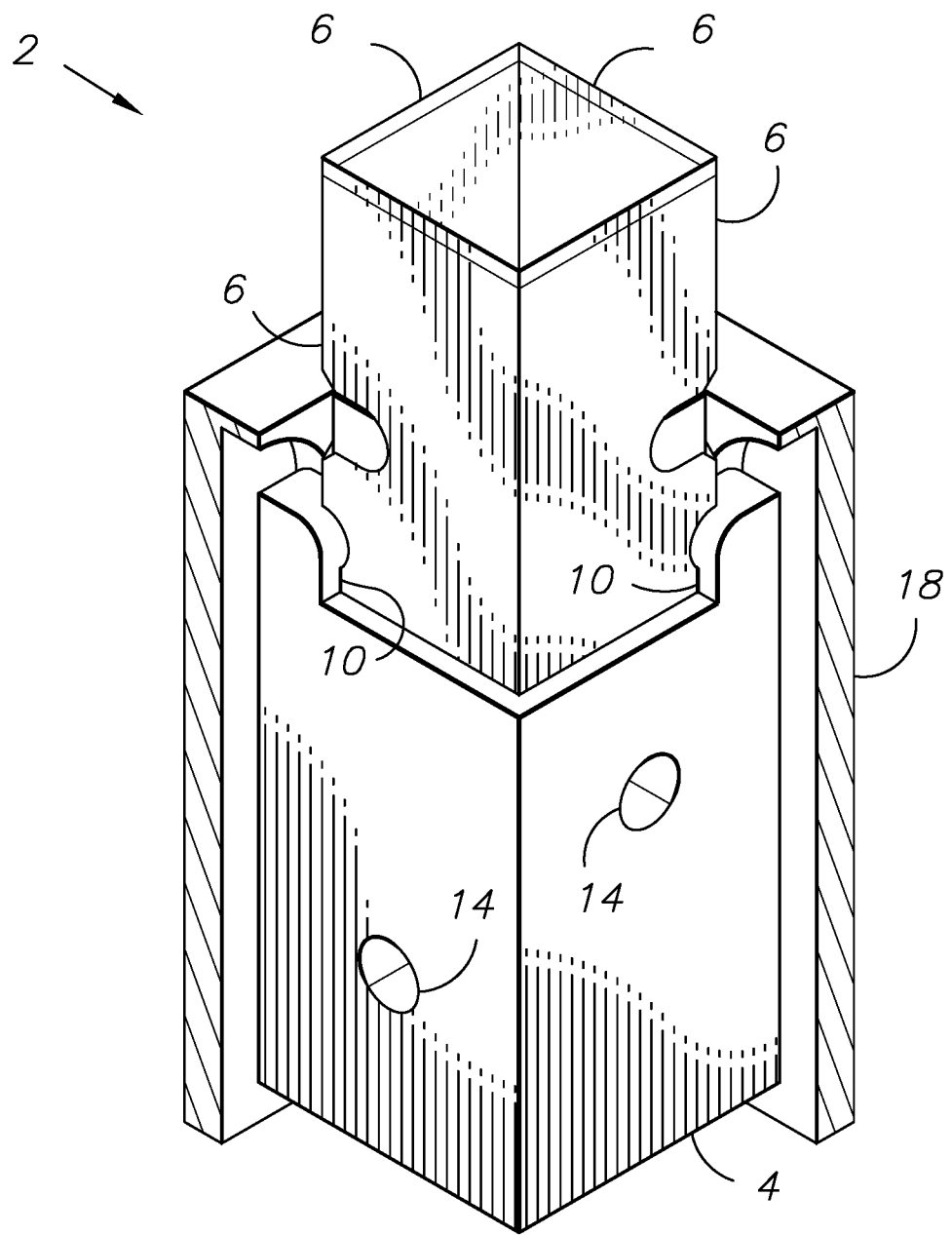
FIG. 8 is an upper, perspective, assembled, cross-sectional view of the biopsy punch device embodying the present invention.
Figure 9:
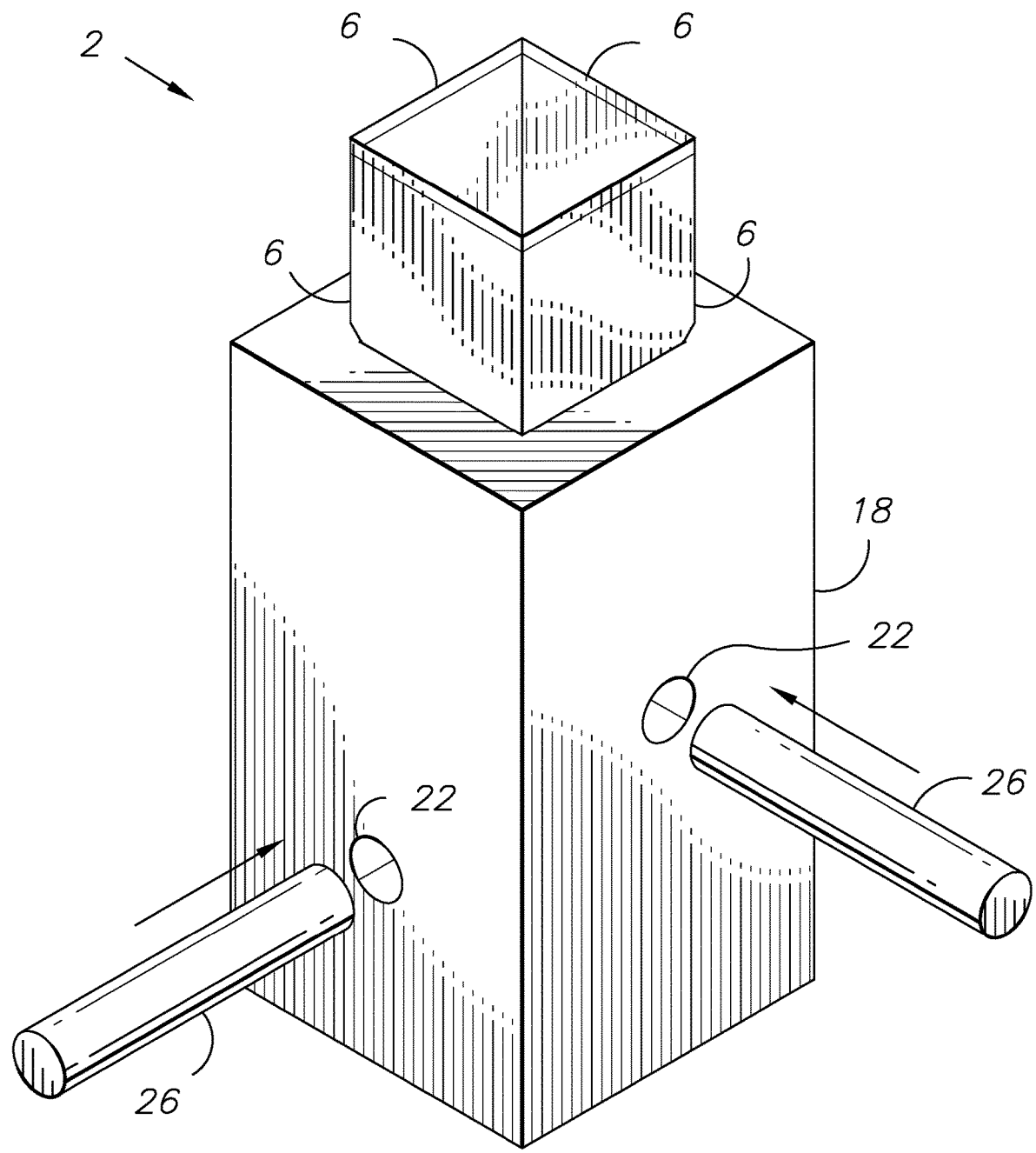
FIG. 9 is an upper, perspective view of the biopsy punch device with the inner housing piece, cutting blades, and blocking cover piece assembled and further showing an exploded view of pins embodying an aspect of the present invention.
Figure 10:
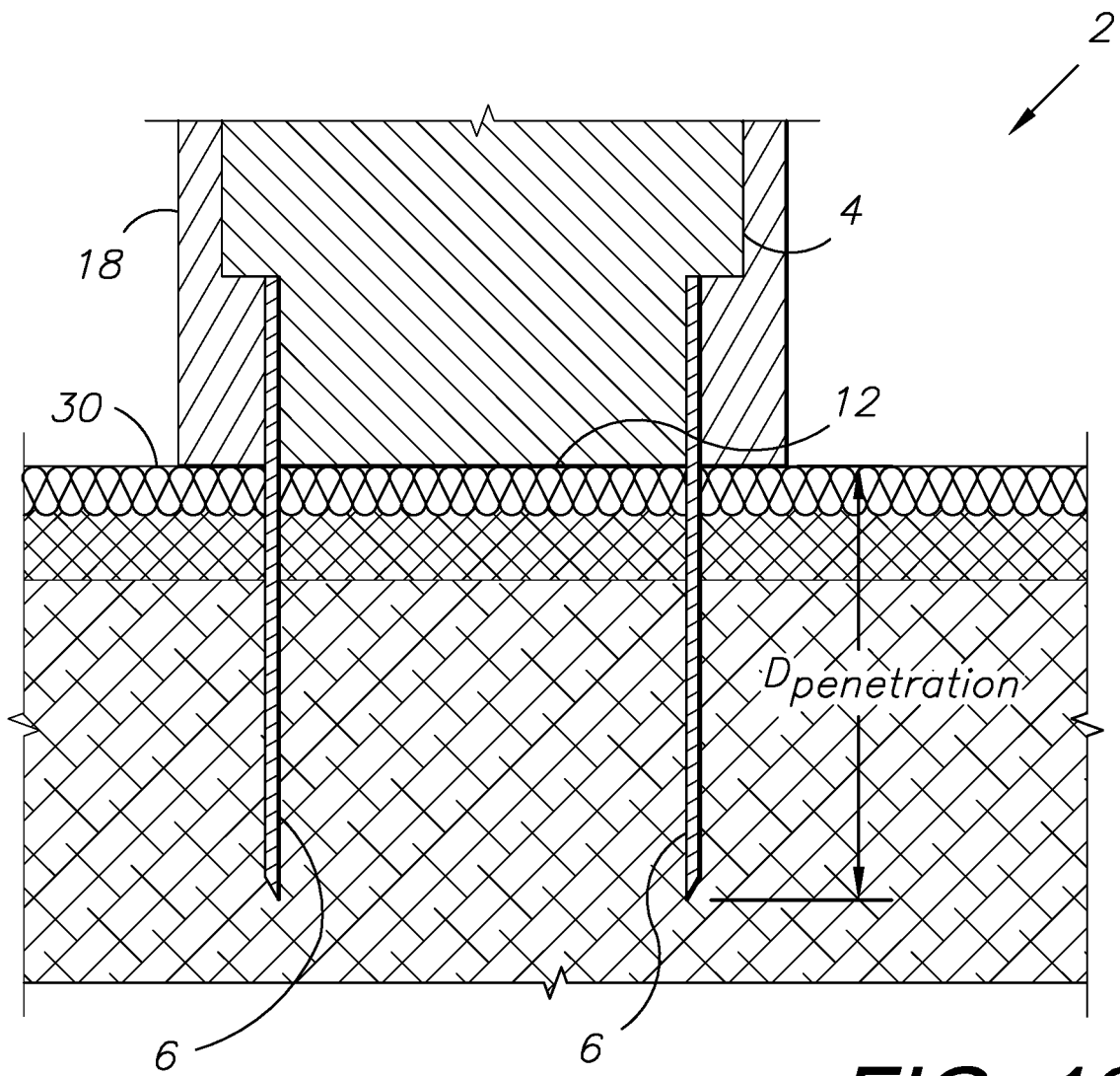
FIG. 10 is a vertical, cross-sectional view of the biopsy punch device of the present invention cutting into a living tissue.

As shown in FIGS. 2-3, the cutting blades 6 in this embodiment are substantially rectangular with first 40 and second 42 ends, the first end 40 being sharpened, and first 44 and second 46 sides connecting the first 40 and second 42 ends. The cutting blades 6 of this embodiment each include a notch 8, such as a notch on a standard, notched, straight-edge razorblade, positioned near the cutting blade second end 42, or the end 42 opposite of the sharpened edge 40. Each cutting blade notch 8 opens toward a first side 44 of the cutting blade. Each notch 8 being open to the cutting blade first side 44 and positioned near the cutting blade second end 42 forms a notch end member 48 along the cutting blade first side 44 between the cutting blade second end 42 and the notch 8. The connection slots 10 in the mounting portion 12 of the housing piece 4, in this embodiment, are configured to receive the cutting blade notch end members 48, as illustrated in FIG. 3, and to hold the cutting blades 6 in place. As further shown in FIG. 3, each connection slot 10 is shaped to closely fit around a cutting blade notch end member 48. The biopsy punch device 2 is configured for easy replacement of cutting blades 6. Alternate embodiments of cutting blade connection slots 10 may further include lugs which allow firm but replaceable fitting of blades 6 specifically designed and cut to fit within the lugs. Further embodiments may include cutting blades 6 permanently affixed into the inner housing piece 4. The inner housing 4 further includes grooves 14 configured to match up with grooves 22 of the blocking cover piece 18 and to receive pins 26 for holding the inner housing 4 and blocking cover 18 in proper relation to each other.

The blocking cover piece 18 of the embodiment shown in FIGS. 1-12 is configured to overlay the inner housing piece 4. The blocking cover piece 18 includes a wider distal end opening 34 and a narrower proximal end opening 20. The blocking cover distal end opening 24 is configured to fit around and adjacent to the inner housing piece distal end 16. The blocking cover proximal end opening 20 is configured to closely fit around the cutting blades 6 and the inner housing mounting portion 12, which further secures the cutting blades 6 in proper position between the inner housing mounting portion 12 and the blocking cover 18.

When fully assembled, the proximal side of the blocking cover piece 18 is configured to expose only a fixed, predetermined length of each cutting blade 6. Thus, the proximal side of the blocking cover piece 18 provides a mechanical stopping feature around the outside of the cutting blades 6 at the fixed depth. In this embodiment, the proximal side of the blocking cover 18 is coplanar with the proximal side of the mounting portion 12 of the housing 4 when the biopsy punch 2 is fully assembled, providing an additional mechanical stopping feature on the inside of the blades 6. However, the blocking cover 18 can provide the stopping feature at a fixed depth on its own. In alternative embodiments, the proximal side of the inner housing mounting portion 12 may be configured to act as the primary mechanical stopping feature of the biopsy punch 2.

Grooves 22 in the blocking cover piece 18, in this embodiment, match up with the inner housing piece grooves 14 and are configured for receiving pins 26. The grooves 14, 22 and pins 26 hold the blocking cover 18, cutting blades 6, and inner housing 4 in proper relation to each other, exposing the fixed, predetermined length of each cutting blade 6. Embodiments of the present invention may include a blocking cover 18 with multiple grooves 22 or settings to allow for stopping penetration of the cutting blades 6 at different predetermined depths. Alternatively, or in combination with different blocking cover 18 settings, the proximal side of the mounting portion 12 of the inner housing 4 may be adjustable, providing a mechanical stop at different predetermined lengths of the cutting blades 6.

Figure 11:
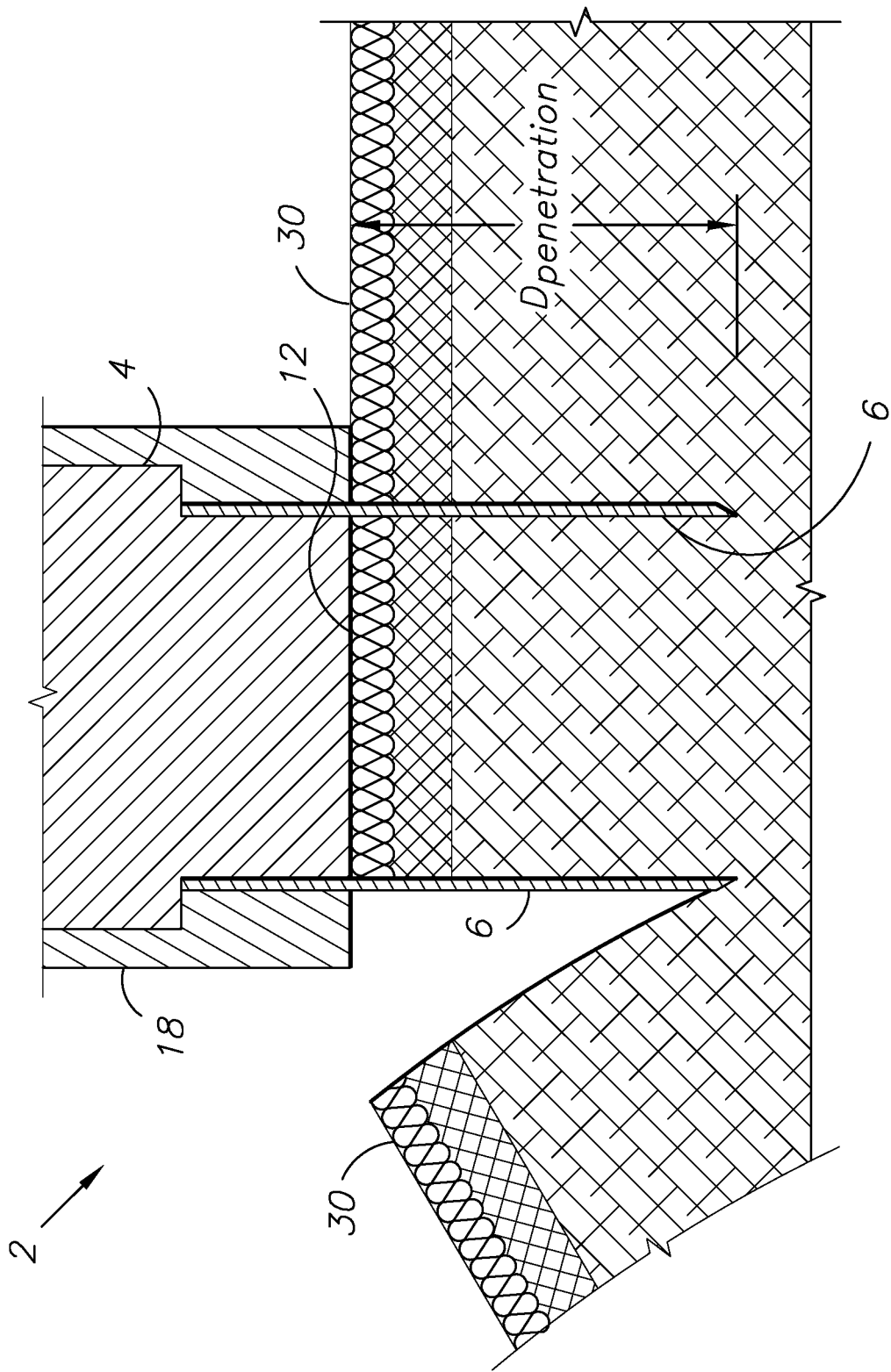
FIG. 11 is a vertical, cross-sectional view of the biopsy punch device cutting into the living tissue, with the tissue being retracted to allow removal of a biopsy tissue sample.
Figure 12:
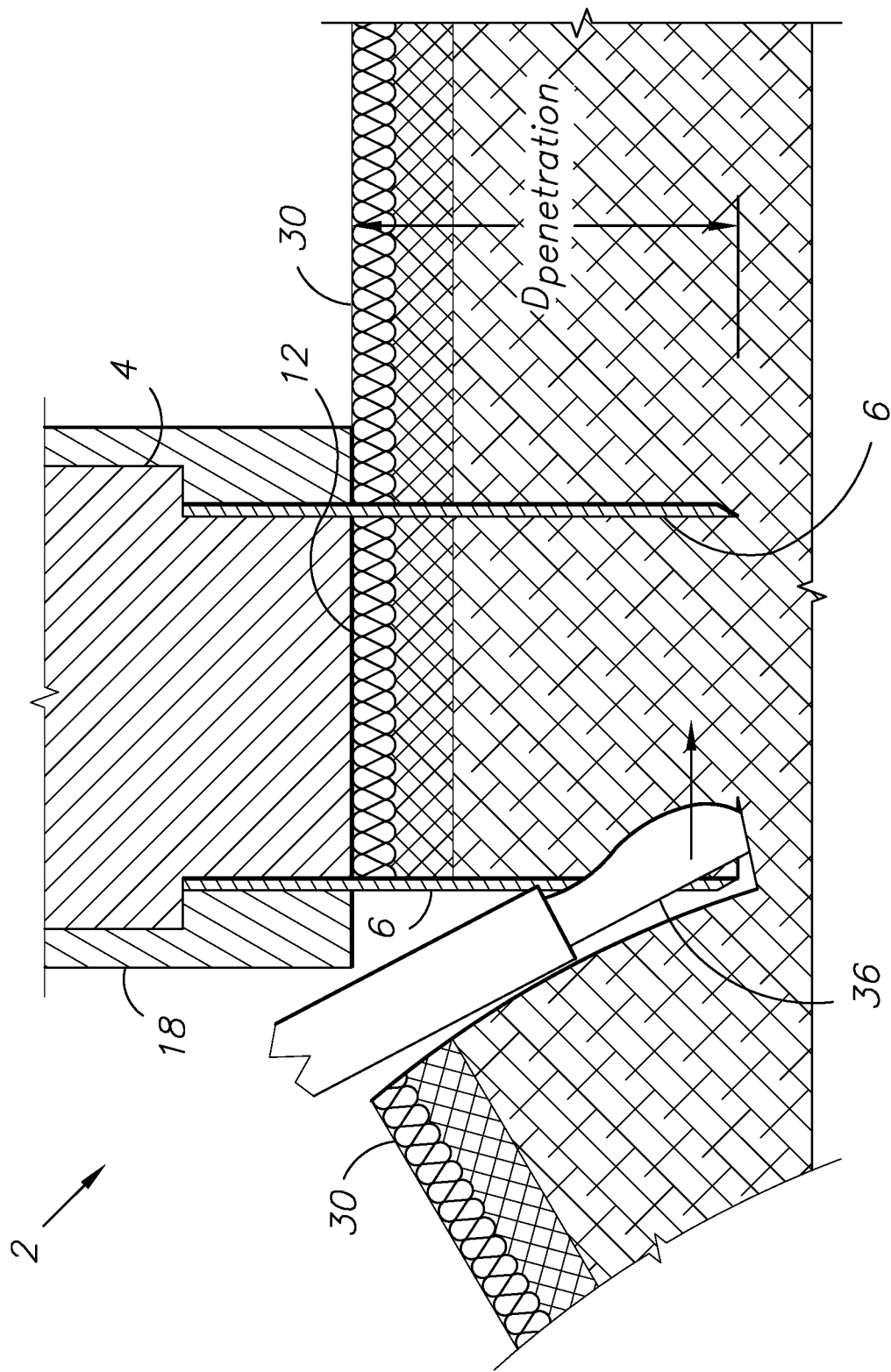
FIG. 12 is a vertical, cross-sectional view of the biopsy punch device cutting into the living tissue, showing a scalpel for cutting the bottom of a biopsy tissue sample.
Figure 13:
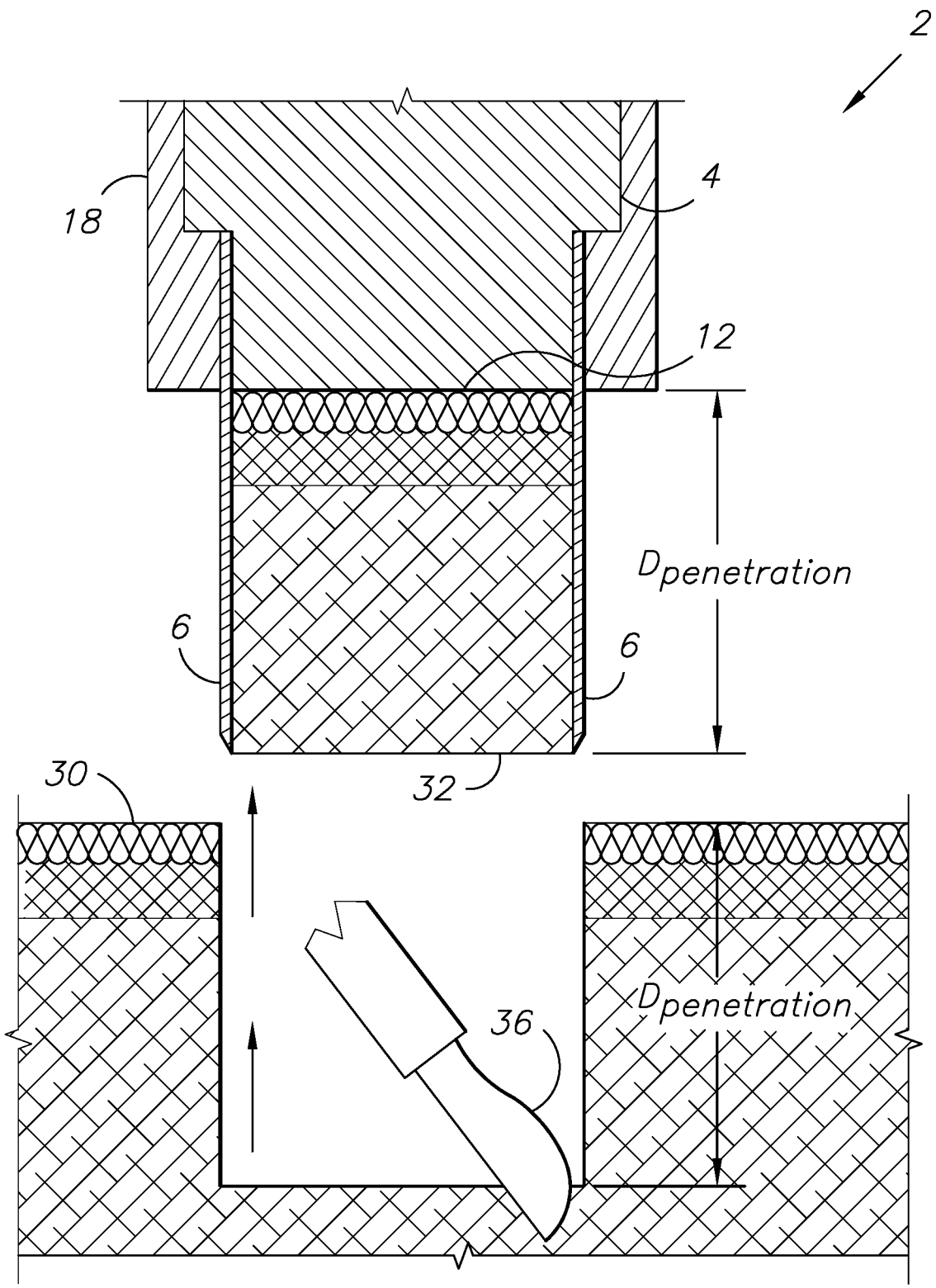
FIG. 13 is a vertical, cross-sectional view of the biopsy tissue sample being removed from the living tissue within the biopsy punch device.
Figure 14:
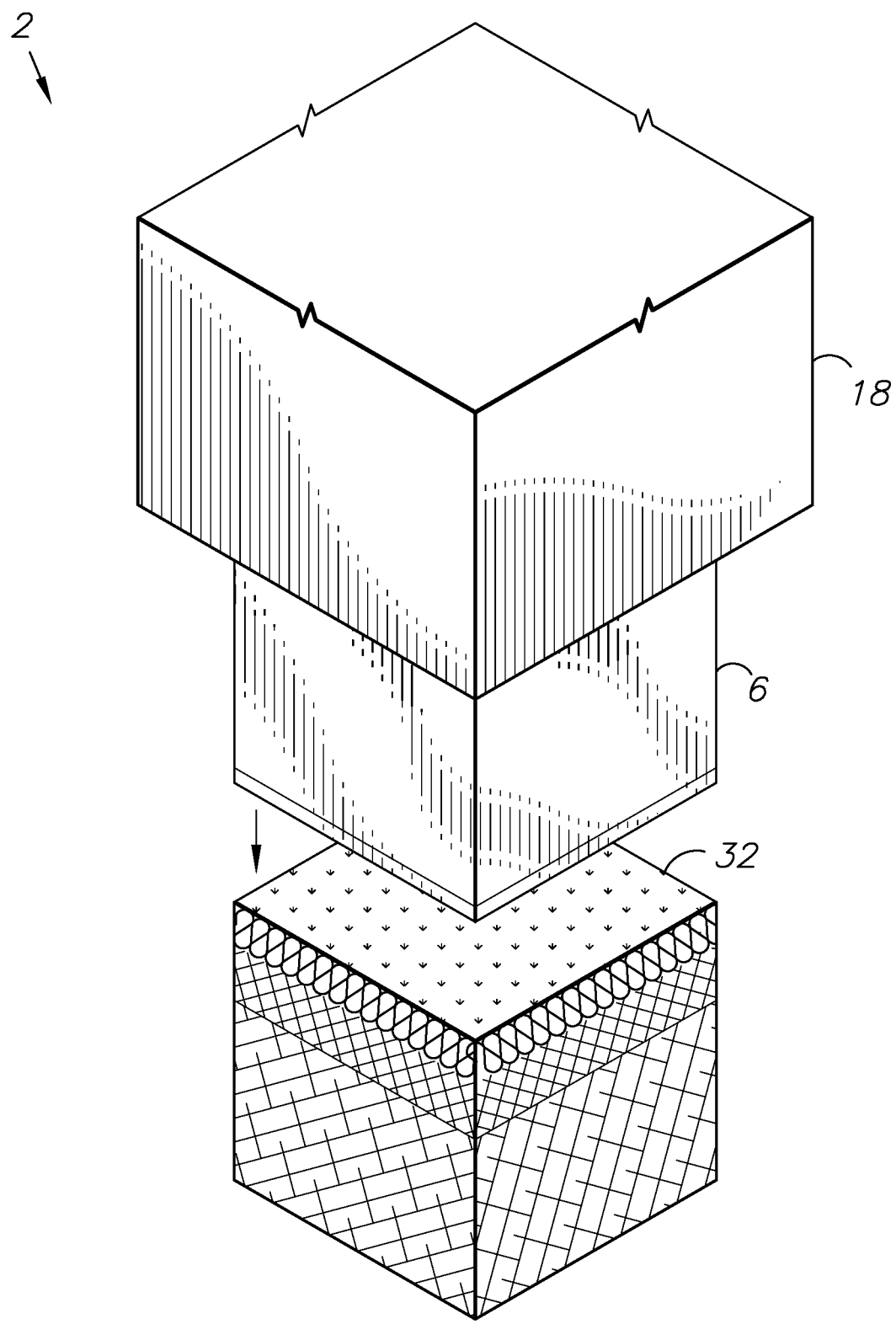
FIG. 14 is an upper, perspective view of a biopsy tissue sample obtained using the biopsy punch device of the present invention.
Figure 15:
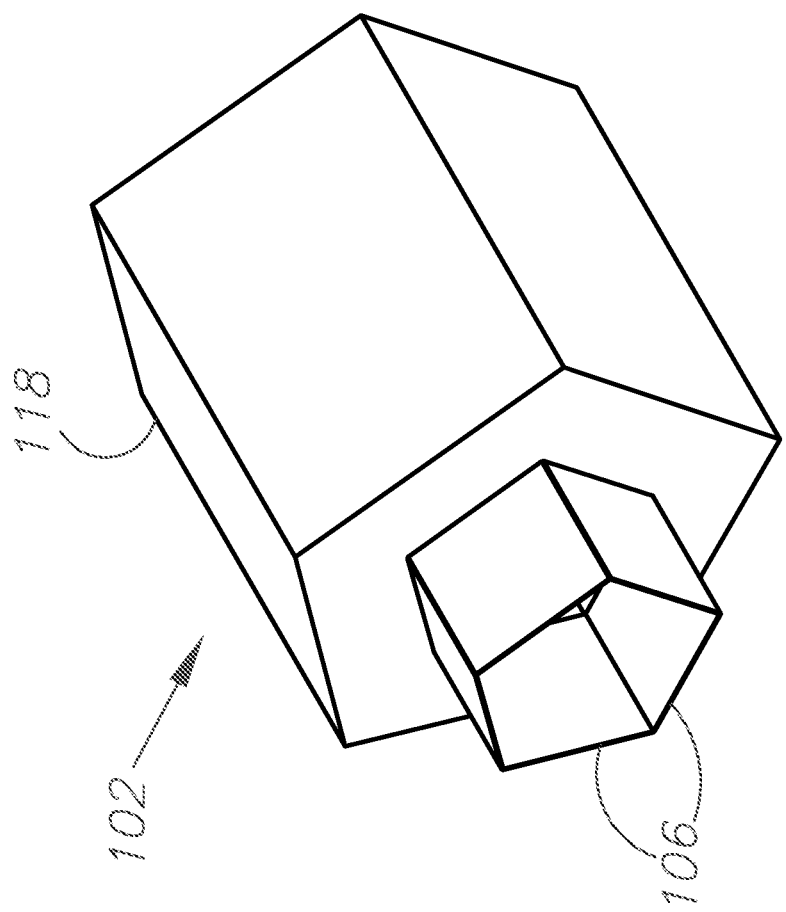
FIG. 15 is a front, perspective, assembled view of an alternative embodiment of a biopsy punch device of the present invention.
Figure 16:
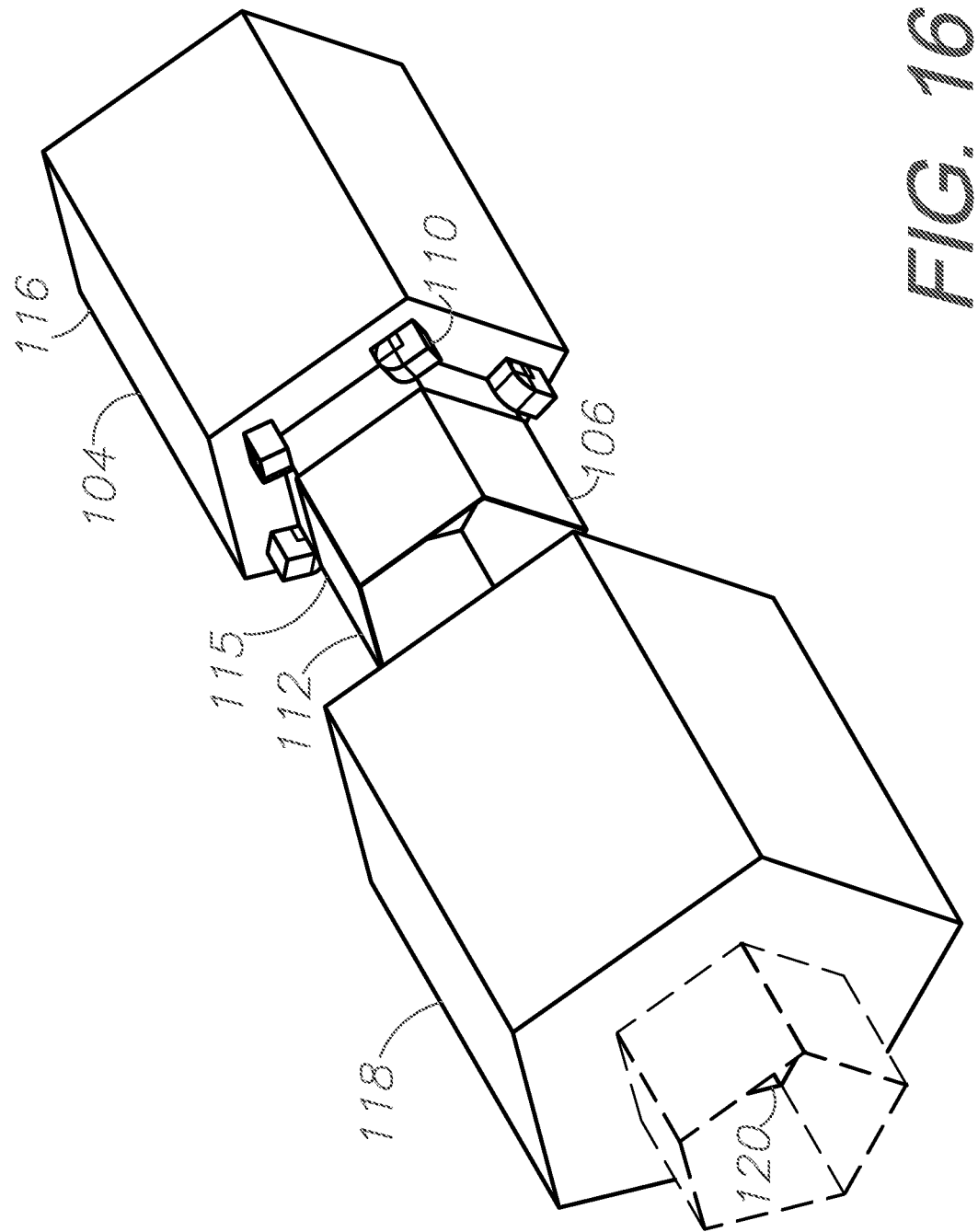
FIG. 16 is a front, perspective, exploded view of the biopsy punch device.
Figure 17:
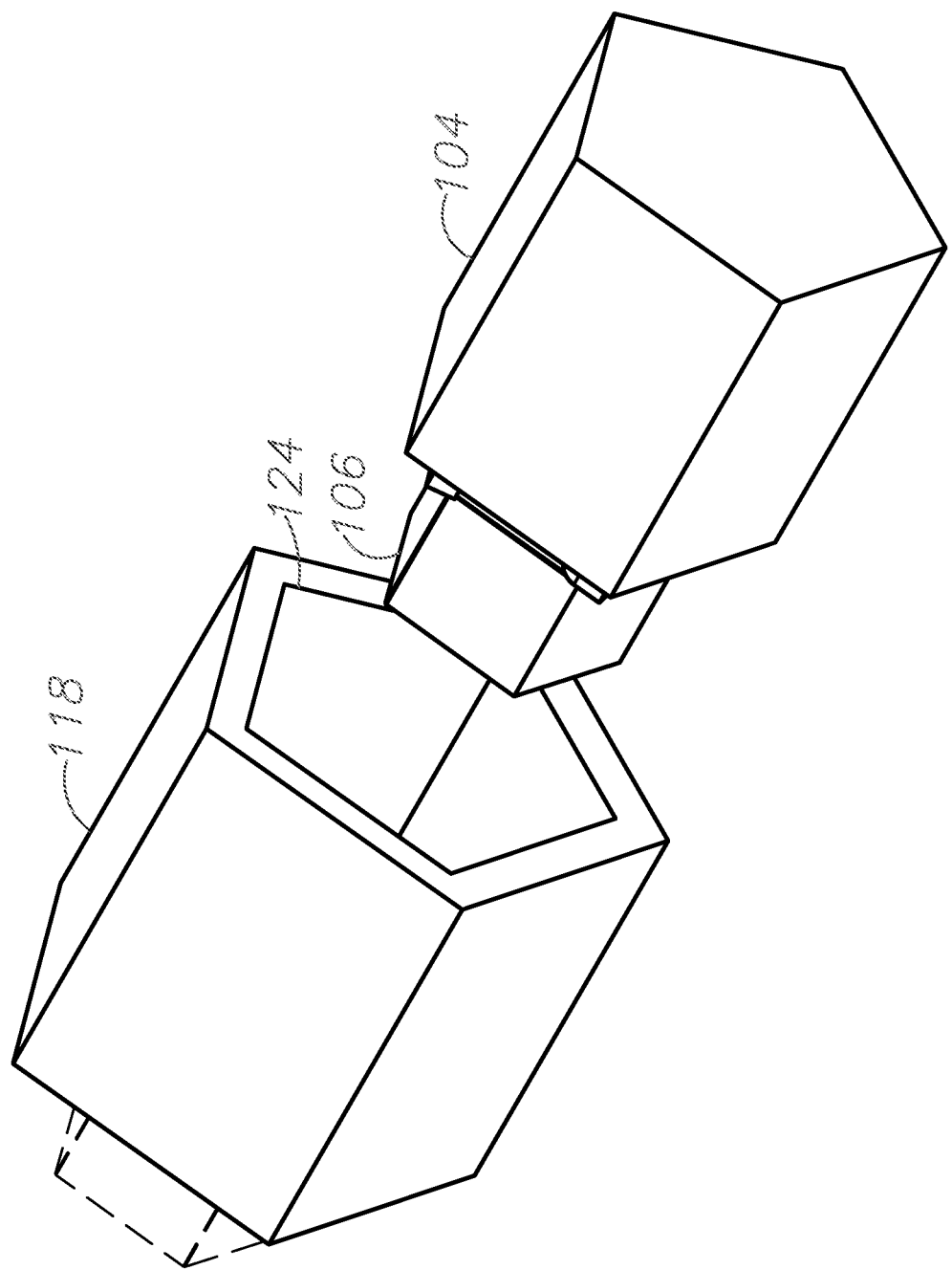
FIG. 17 is a back, perspective, exploded view of the biopsy punch device.
Figure 18:
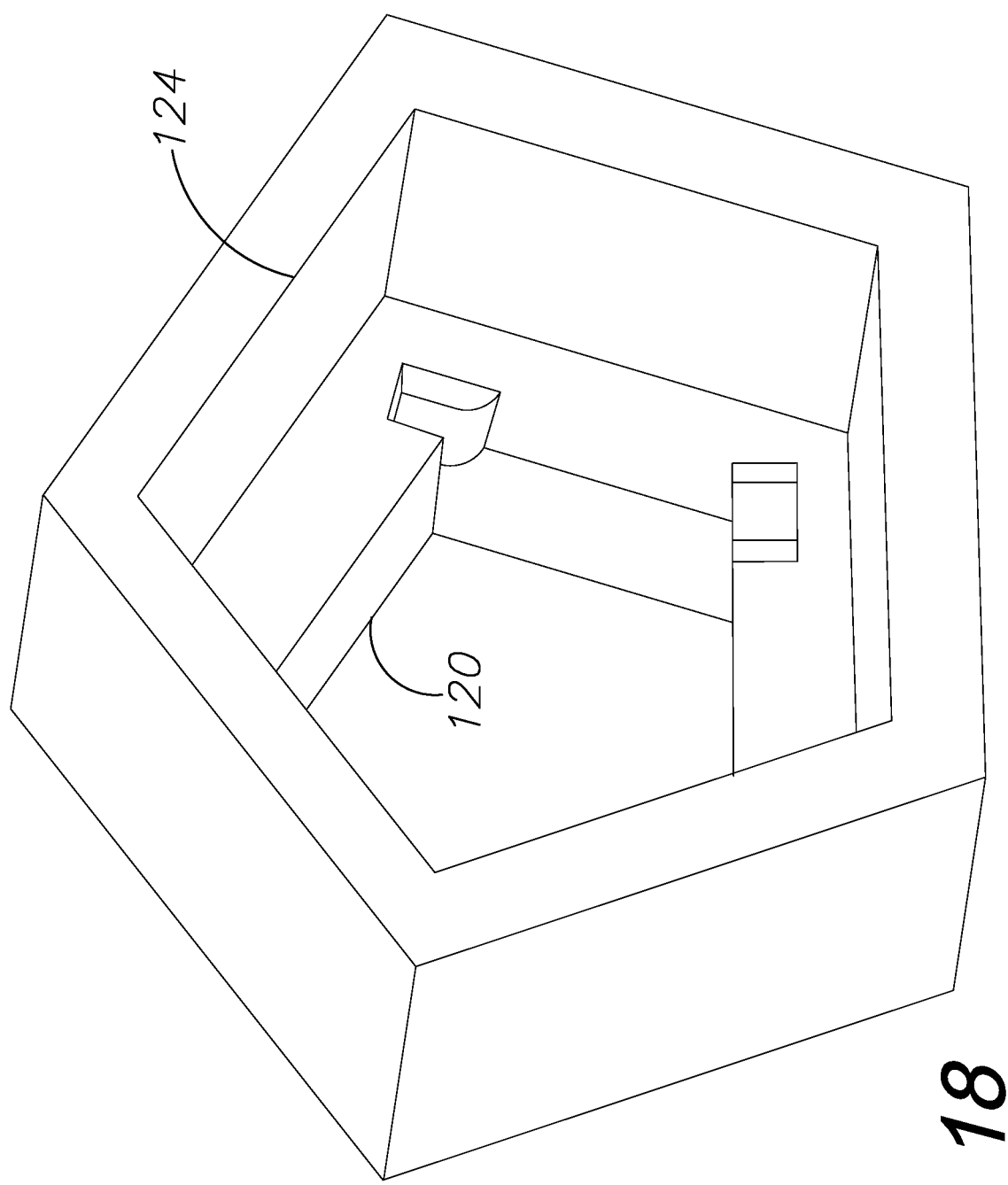
FIG. 18 is a bottom, perspective view of the blocking cover piece of the biopsy punch device.

FIGS. 10-13 show vertical, cross-sectional views of the biopsy punch 2 used to punch cut living tissue 30 and obtain a biopsy tissue sample 32. The cutting blades 6 of the biopsy punch device 2 are configured for cutting into the tissue 30 at a fixed depth of penetration $D_{penetration}$. The proximal side, or blocking feature, of the blocking cover piece 18 causes a mechanical stop of the punch cut at the fixed depth of penetration $D_{penetration}$, forming a biopsy tissue sample 32 between the cutting blades 6. The biopsy tissue sample 32 can then be severed at the base. With the tissue sample 32 within the cutting blades 6, tissue 30 adjacent and outside the cutting blades 6 can be retracted, as shown in FIG. 11. A scalpel 36 can then be inserted and used to sever the base of the tissue sample 32 against the edge of the blades 6, maintaining the proper depth, to remove the tissue sample from the living organism, as shown in FIGS. 12-13. Alternatively, the biopsy punch 2 can be removed and the base of the tissue sample 32 cut with tissue scissors, preferably curved, with the tissue scissors placed at the depth of the biopsy punch 2 cuts to sever the base of tissue sample 32 at the appropriate predetermined depth. FIG. 14 shows an isometric view of the biopsy tissue sample 32 obtained with the biopsy punch device 2. The biopsy tissue sample 32 can then be used for medical testing and/or research purposes.

FIGS. 15-18 show an alternative embodiment of a biopsy punch device 102 having cutting blades 106 arranged in a pentagon shape. This embodiment is configured to produce pentagonal prism punch biopsy samples with a fixed depth of penetration of the cutting blades 106. The biopsy punch device 102 includes an inner housing piece 104 and a blocking cover piece 118 configured to overlay the housing piece 104. The inner housing piece 104 has a wider distal end 116 and a narrower proximal end 115 including a mounting portion 112. The mounting portion 112, in this embodiment, is a pentagon shape and includes five connection or receiving slots 110, one positioned at each corner of the pentagon shape, for receiving and holding five cutting blades 106 arranged in a pentagon configuration.

In this embodiment, the blocking cover piece 118 includes a wider distal end opening 124 and a narrower proximal end opening 120. The blocking cover distal end opening 124 is configured to fit around and adjacent to the inner housing piece distal end 116. The blocking cover proximal end opening 120 is configured to closely fit around the cutting blades 106 and the inner housing mounting portion 112, which further secures the cutting blades 106 in proper position between the inner housing mounting portion 112 and the blocking cover 118.

In an assembled configuration, the proximal side of the blocking cover piece 118 is configured to expose a fixed, predetermined length of each cutting blade 106. The proximal side of the blocking cover piece 118 provides a mechanical stopping feature around the outside of the cutting blades 106 at the desired fixed depth, allowing for consistent, reproducible, fixed depth biopsy samples.

Figure 19:
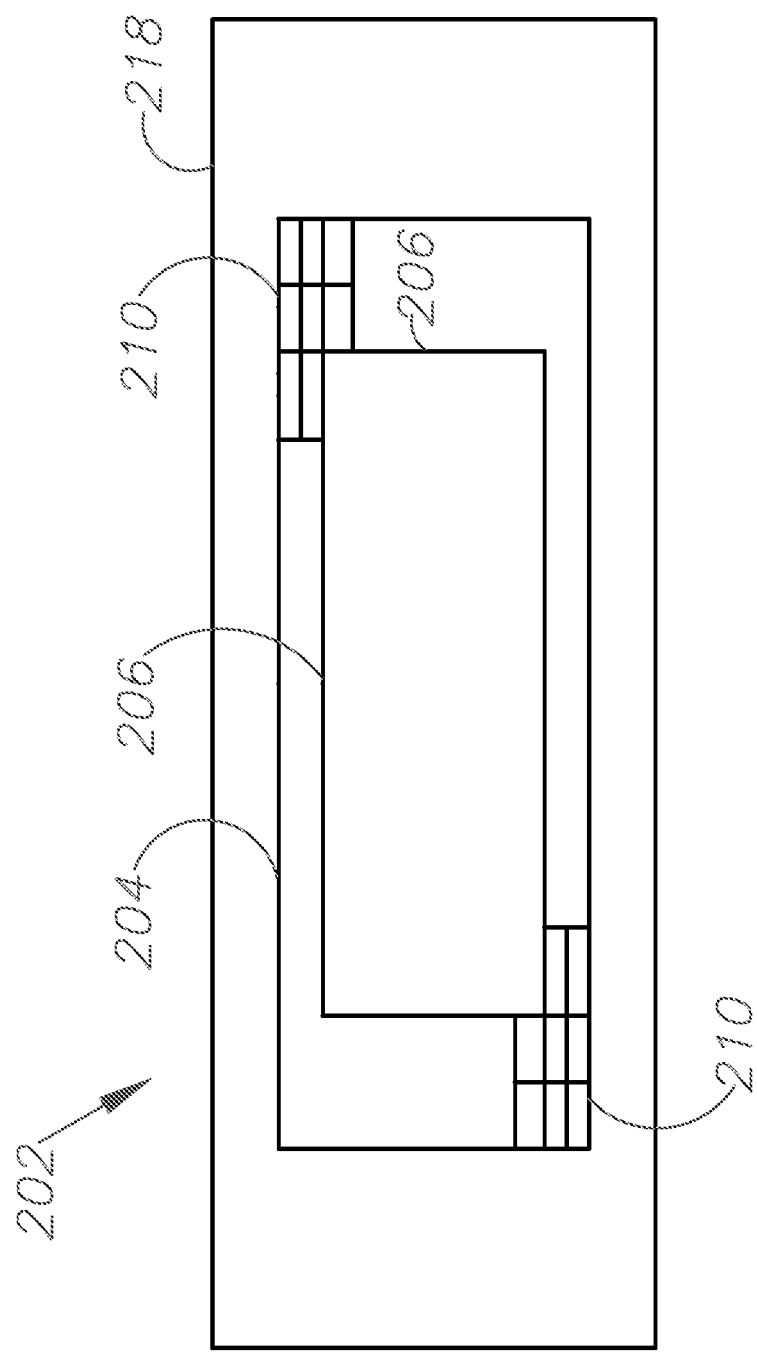
FIG. 19 is a top, plan view of another alternative embodiment of a biopsy punch device of the present invention.

FIG. 19 shows an alternative embodiment of a biopsy punch device 202 of the present invention having cutting blades 206 arranged in a rectangle shape. In this embodiment, the biopsy punch device 202 is configured to produce rectangular prism punch biopsy samples with a fixed depth of penetration of the cutting blades 206. The cutting blades 206 in this embodiment have differing widths, with two sides having wider cutting blades and two sides having narrower cutting blades. The biopsy punch device 202 includes an inner housing piece 204 having cutting blade connection slots 210 configured for releasably mounting the cutting blades 206 and a blocking cover piece 218 configured for overlaying the inner housing piece 204 and fitting around and adjacent to the cutting blades 206. The blocking cover 218 is configured for providing a mechanical stop in the cutting process at a desired fixed depth.

FIG. 20 shows an elevational view of an embodiment of a biopsy punch device 302 of the present invention including a blocking cover extension attachment 340. The blocking cover extension attachment 340 allows for an alternative fixed cutting depth setting of the biopsy punch device 302 in addition to the cutting depth of the biopsy punch device 302 without the extension attachment 340 attached. The blocking cover extension attachment 340 includes proximal and distal ends with an opening therethrough. The blocking cover extension opening is configured to correspond in size to the blocking cover proximal opening. The distal side of the extension attachment 340 is configured for connecting to the proximal side of the blocking cover 318 and to fit around and adjacent to the cutting blades 306. In this embodiment, the proximal side of the extension attachment 340 provides a mechanical stop during the cutting process at a desired alternative fixed cutting depth.

In addition to manual biopsy punch devices and methods, alternative embodiments of the present invention include automated, machine-controlled punch cut devices and methods. The biopsy punch device of the present invention can be commonly used for clinical excisions and for biopsies of human tissue; strip harvests of human tissue for grafting or transplant purposes; animal therapy; and animal laboratory experimental protocols. However, the present invention can be further adapted for other types of fixed depth punch tools. Such further embodiments could include fixed depth drills; augers; punch tools for working with leather, metal, or other materials; cookie cutters; stamping machines; and any other types of punch tools.

It is to be understood that the invention can be embodied in various forms and is not to be limited to the examples specifically discussed. The range of components and configurations which can be utilized in the practice of the present invention is virtually unlimited.

Having thus described the invention, what is claimed as new and desired to be secured by Letters Patent is:

1. A biopsy punch device comprising:
    a housing member having first and second ends;
    said housing member first end releasably mounting a plurality of cutting blades extending outwardly therefrom, each said cutting blade having first and second ends and first and second sides connecting said cutting blade first and second ends;
    each said cutting blade comprising a notch open to said cutting blade first side and positioned near said cutting blade second end;
    wherein each said notch and each said cutting blade second end form a notch end member;
    said housing member first end further comprising a plurality of cutting blade receiving slots configured for releasably mounting and holding said cutting blades in a fixed position;
    wherein each said cutting blade receiving slot is shaped to closely fit around said notch end member of one of said cutting blades and configured to hold one of said cutting blades in said fixed position;
    wherein in an assembled configuration said cutting blades are arranged such that said first ends of said cutting blades form a planar, multisided geometric shape;
    each said cutting blade first end having a sharpened outer edge and configured for cutting tissue;
    a blocking cover having first and second ends with first and second openings;
    said blocking cover configured for overlaying said housing member in said assembled configuration;
    said blocking cover second opening configured for fitting in covering relation around said housing member second end in said assembled configuration;
    said blocking cover first opening configured for fitting around and adjacent to said cutting blades in said assembled configuration; and
    said cutting blades extending outwardly from the first end of said blocking cover in said assembled configuration an extension length.

2. The biopsy punch device according to claim 1, wherein:
    said extension length of said cutting blades corresponds to a desired fixed cutting depth;
    said blocking cover first end is configured for making contact with tissue surrounding a tissue to be sampled and for providing a mechanical stop in the cutting process at said desired fixed cutting depth; and
    said biopsy punch device is configured for cutting a biopsy tissue sample in a geometric prism shape having ends corresponding to said multisided geometric shape and having a depth corresponding to said desired fixed cutting depth.

3. The biopsy punch device according to claim 1, further comprising:
    a stop mechanism configured for releasably locking said blocking cover in relation to said housing member and said cutting blades in said assembled configuration.

4. The biopsy punch device according to claim 3, wherein:
    said stop mechanism comprises a locking mechanism selected from the group consisting of: grooves and pin; a snapping actuator; magnet; hooks; and an internal receiver and stopper.

5. The biopsy punch device according to claim 3, wherein:
    said biopsy punch device includes multiple assembled configuration settings configured for multiple fixed cutting depths.

6. The biopsy punch device according to claim 5, wherein:
    said stop mechanism includes multiple, adjustable stop settings configured for releasably locking said blocking cover in relation to said housing member and said cutting blades in each of said multiple assembled configuration settings.

7. The biopsy punch device according to claim 5, further comprising:
    a blocking cover extension attachment having first and second ends with an opening therethrough corresponding in size to said blocking cover first opening;
    said blocking cover extension attachment configured for fitting around and adjacent to said cutting blades and extending outwardly from said blocking cover first end in an extension attachment assembled configuration; and
    said cutting blades extending outwardly from the first end of said blocking cover extension attachment in said extension attachment assembled configuration a blade extension length corresponding to a desired alternative fixed cutting depth.

8. The biopsy punch device according to claim 1, wherein:
    said geometric shape is selected from the group consisting of: a square, a rectangle, a triangle, a pentagon, a hexagon, and an octagon.

9. A biopsy punch device comprising:
    a housing member having first and second ends;
    said housing member first end being narrower than said housing member second end and comprising a plurality of cutting blade receiving slots configured for releasably mounting and holding a plurality of straightedge cutting blades of equal length in a fixed position;
    said cutting blades each having first and second ends and first and second sides connecting said cutting blade first and second ends;
    each said cutting blade comprising a notch open to said cutting blade first side and positioned near said cutting blade second end;
    wherein each said notch and each said cutting blade second end form a notch end member;
    wherein each said cutting blade receiving slot is shaped to closely fit around said notch end member of one of said cutting blades and configured to hold one of said cutting blades in said fixed position;
    wherein in an assembled configuration said cutting blades are arranged such that said first ends of said cutting blades form a planar, multisided geometric shape;

each said cutting blade first end having a sharpened outer edge;
said cutting blades configured for cutting tissue;
a blocking cover having first and second ends with first and second openings;
said blocking cover configured for overlaying said housing member in said assembled configuration;
wherein said blocking cover second opening is wider than said blocking cover first opening and configured for fitting in covering relation around said housing member second end in said assembled configuration;
said blocking cover first opening configured for fitting around and adjacent to said cutting blades in said assembled configuration;
said cutting blades extending outwardly from the first end of said blocking cover in said assembled configuration an extension length corresponding to a desired fixed cutting depth;
said housing member comprising grooves configured for matching up with grooves on said blocking cover in said assembled configuration;
said housing member grooves and said blocking cover grooves configured for receiving a pin;
a pin configured for insertion into said housing member grooves and said blocking cover grooves and releasably locking said blocking cover in relation to said housing member and said cutting blades in said assembled configuration;
said blocking cover first end configured for making contact with tissue surrounding a tissue to be sampled and for providing a mechanical stop in the cutting process at said desired fixed cutting depth;
said biopsy punch device configured for cutting biopsy tissue samples in a geometric prism shape having ends corresponding to said multisided geometric shape and having a depth corresponding to said desired fixed cutting depth; and
wherein said geometric shape is selected from the group consisting of: a square, a rectangle, a triangle, a pentagon, a hexagon, and an octagon.

10. A method of obtaining a punch biopsy tissue sample from a living tissue using a biopsy punch device including a housing member having first and second ends; the housing member first end including a plurality of cutting blade receiving slots each configured for receiving, releasably mounting, and holding a cutting blade in a fixed position; a blocking cover having first and second ends with first and second openings and configured for overlaying the housing member in an assembled configuration; and a stop mechanism configured for releasably locking the blocking cover in relation to the housing member in the assembled configuration, the method comprising the steps of:
providing a plurality of cutting blades, each cutting blade having first and second ends and first and second sides connecting said cutting blade first and second ends;
wherein each said cutting blade further comprises a notch open to said cutting blade first side and positioned near said cutting blade second end;
wherein each said notch and each said cutting blade second end form a notch end member;
placing each said cutting blade notch end member within one of said cutting blade receiving slots such that said first ends of said cutting blades form a planar, multisided geometric shape in said assembled configuration;
said cutting blade receiving slots fixedly holding said cutting blades in fixed position;
placing said blocking cover over said housing member and said cutting blades with said blocking cover second opening fitting in covering relation around said housing member second end and said blocking cover first opening fitting around and adjacent to said cutting blades;
said stop mechanism locking said blocking cover in relation to said housing member and said cutting blades with said cutting blades extending outwardly from the first end of said blocking cover an extension length corresponding to a desired fixed cutting depth;
cutting a tissue with said cutting blades;
said blocking cover first end making contact with tissue surrounding said tissue being cut and providing a mechanical stop in the cutting process at said desired fixed cutting depth; and
obtaining a biopsy tissue sample in a geometric prism shape having ends corresponding to said multisided geometric shape and having a depth corresponding to said desired fixed cutting depth.

11. The method according to claim 10, further comprising the steps of:
cutting out said biopsy tissue sample from surrounding tissue; and
removing said biopsy tissue sample from said biopsy punch device.

12. The method according to claim 10, further comprising the steps of:
removing said blocking cover;
removing said cutting blades from said cutting blade receiving slots; and
replacing said removed cutting blades with new notched cutting blades.

13. The method according to claim 10, further comprising the step of:
adjusting said stop mechanism to an alternate assembled configuration setting with said blocking cover in a desired alternate position in relation to said housing member and said cutting blades.

14. The method according to claim 10, further comprising the steps of:
providing a blocking cover extension attachment having first and second ends with an opening therethrough corresponding in size to said blocking cover first opening;
placing said blocking cover extension attachment around and adjacent to said cutting blades extending outwardly from said blocking cover first end; and
said blocking cover extension attachment first end providing a mechanical stop in the cutting process at a desired alternative fixed cutting depth.

* * * * *